US012751615B2

(12) United States Patent
Davies et al.

(10) Patent No.: US 12,751,615 B2
(45) Date of Patent: Oct. 6, 2026

(54) VIRTUAL REALITY TECHNIQUES FOR CHARACTERIZING VISUAL CAPABILITIES

(71) Applicant: HOFFMANN-LA ROCHE INC., Little Falls, NJ (US)

(72) Inventors: Geraint Iwan Davies, Leymen (FR); Jonas Franz Dorn, Muenchenstein (CH); Bernhard Fehlmann, Wuerenlos (CH); Noémie Hurst-Fischer, Turckheim (FR); Angelos Karatsidis, Rheinfelden (CH); Joerg Sprengel, Muellheim (DE)

(73) Assignee: HOFFMANN-LA ROCHE INC., Little Falls, NJ (US)

( * ) Notice: Subject to any disclaimer, the term of this patent is extended or adjusted under 35 U.S.C. 154(b) by 269 days.

(21) Appl. No.: 18/542,893

(22) Filed: Dec. 18, 2023

(65) Prior Publication Data

US 2024/0122469 A1 Apr. 18, 2024

Related U.S. Application Data

(63) Continuation of application No. PCT/US2022/032180, filed on Jun. 3, 2022.
(Continued)

(51) Int. Cl.
*A61B 3/113* (2006.01)
*A61B 3/00* (2006.01)
(Continued)

(52) U.S. Cl.
CPC ............ *A61B 3/113* (2013.01); *A61B 3/0025* (2013.01); *A61B 3/005* (2013.01); *A61B 5/1114* (2013.01);
(Continued)

(58) Field of Classification Search
CPC .. A61B 3/00; A61B 3/005; A61B 3/11; A61B 3/113; A61B 3/0025; A61B 3/02;
(Continued)

(56) References Cited

U.S. PATENT DOCUMENTS

2017/0262049 A1 9/2017 Kim
2017/0273552 A1 9/2017 Leung et al.
2019/0391638 A1 12/2019 Khaderi et al.

FOREIGN PATENT DOCUMENTS

JP 2015502238 A 1/2015
JP 2019513516 A 5/2019
(Continued)

OTHER PUBLICATIONS

PCT/US2022/032180 , "International Search Report and Written Opinion", issued by the European Patent Office, as International Searching Authority on Sep. 23, 2022, 10 pages.
(Continued)

*Primary Examiner* — Jie Lei
(74) *Attorney, Agent, or Firm* — Kilpatrick Townsend & Stockton LLP

(57) ABSTRACT

A virtual reality system for quantifying functional visual capabilities of a user at varying assessment conditions (e.g., varying light, contrast, color conditions), using a head-mountable display. In addition to the high relevance to users with optical conditions, the present embodiments can lead to rapid and simple measurements within the controlled and reproducible testing conditions that virtual reality can offer. The virtual environment system can obtain a selection of a task to be performed. During execution of the task, a virtual environment optical setting (e.g., a modified lighting setting in the virtual environment display) can be dynamically modified. The user can interact with the objects during execution of the task, which can provide an insight into functional visual capabilities of the user. After completion of
(Continued)

the task, an output can be generated that quantifies a functional visual capability of the user during execution of the task.

20 Claims, 6 Drawing Sheets

Related U.S. Application Data

(60) Provisional application No. 63/211,930, filed on Jun. 17, 2021.

(51) Int. Cl.

| | |
|---|---|
| ***A61B 5/00*** | (2006.01) |
| ***A61B 5/11*** | (2006.01) |
| ***G06F 3/01*** | (2006.01) |

(52) U.S. Cl.
CPC ............ *A61B 5/6803* (2013.01); *G06F 3/012* (2013.01); *G06F 3/013* (2013.01)

(58) Field of Classification Search
CPC .. A61B 3/10; A61B 3/112; A61B 5/00; A61B 5/11; A61B 5/1114; A61B 5/6803; G02B 7/02; G02B 7/12; G02B 7/023; G02B 7/026; G02B 25/00; G02B 25/001; G02B 27/01; G02B 27/017; G02B 27/0172; G02B 27/0176; G02B 2027/0154; G06F 3/01; G06F 3/012; G06F 3/013; G06F 3/011
USPC .................. 359/13, 630–633, 815, 480, 481; 351/209, 200, 211, 210, 245, 246
See application file for complete search history.

(56) References Cited

FOREIGN PATENT DOCUMENTS

| | | | |
|---|---|---|---|
| JP | 2019166101 | A | 10/2019 |
| JP | 2019535401 | A | 12/2019 |
| JP | 2020156956 | A | 10/2020 |
| JP | 2021502881 | A | 2/2021 |
| WO | 2018199196 | A1 | 11/2018 |

OTHER PUBLICATIONS

Application No. KR10-2023-7045464, Office Action, Mailed on Jul. 31, 2025, 13 pages.

VIRTUAL REALITY TECHNIQUES FOR CHARACTERIZING VISUAL CAPABILITIES

CROSS-REFERENCE TO RELATED APPLICATIONS

The present application is a U.S. Continuation of International Application No. PCT/US2022/032180, filed Jun. 3, 2022, which claims the benefit of and the priority to U.S. Provisional Application No. 63/211,930, filed on Jun. 17, 2021, the entire contents of which are herein incorporated by reference in their entireties for all purposes.

BACKGROUND

Various optical conditions (e.g., eye diseases) can limit portions of the vision of an individual. For example, retinitis pigmentosa, an inherited retinal disease, can primarily affect night vision and peripheral vision and can lead to loss of central vision and legal blindness. As another example, geographic atrophy or Stargardt disease can first reduce central vision of an individual prior to loss of other visual capabilities of the individual.

In many instances, only central vision loss is routinely assessed in the clinic by performing a test such as a best corrected visual acuity test. Although this test is well established, it can fail to detect optical conditions that can also affect subjects in their everyday life, such as vision in low light. To address such limitations, a test such as a best corrected visual acuity test can be supplemented with one or more other assessments, such as an electroretinography, dark adaptometry, or perimetry assessment. However, the combination of assessments can be time consuming, cumbersome to subjects and care providers, and may require special resources. Consequently, such assessments are typically performed once at most, such as at the time of diagnosis. Additionally, even the combination of assessments may fail to capture the degree to which a subject's vision is functionally impaired.

SUMMARY

Some embodiments of the present disclosure are directed to providing a virtual reality environment that presents a visual scene implementing a task and that facilitates tracking a user's interaction with the environments (e.g., via sensor data). The interactions are transformed into an output that assesses a degree to which the subject's vision is functionally impaired.

More specifically, disclosed herein are techniques for implementing a task to be performed in a virtual reality environment, deriving a performance metric during execution of the task, and generating an output that quantifies a functional visual capability of a user based on performance during the implementation of the task. Optical characteristics can be dynamically modified during implementation of the task to modify optical features of the virtual reality environment, which can further identify functional visual capabilities of a user. Various embodiments are described herein, including devices, systems, modules, methods, non-transitory computer-readable storage media storing programs, code, or instructions executable by one or more processors, and the like.

According to certain embodiments, a method for measuring functional visual capabilities of a user in a virtual reality environment is provided, such as an object selection task, an object interaction task, or a reading task. The method can include identifying a task to be implemented in the virtual reality environment. The virtual reality environment can be displayed by a head-mountable display. Display of the virtual reality environment can include at least one optical setting that is dynamically modified during implementation of the task. The method can also include facilitating implementation of the task. Implementation of the task can include displaying a plurality of virtual objects on the display of the VR environment by the head-mountable display.

The method can also include obtaining, during implementation of the task, a set of sensor data from a set of sensors. The method can also include processing the set of sensor data to map a first set of coordinates representing movements in the virtual reality environment directed by the user with a second set of coordinates specifying locations of the dynamic virtual objects in the virtual reality environment. The method can also include deriving a first performance metric based on the mapped coordinates. The method can also include generating an output based on the first performance metric. The output can quantify a functional visual capability of the user.

According to certain embodiments, a virtual environment system is provided. The virtual environment system can include a head-mountable display configured to display a virtual reality environment. The virtual environment system can also include one or more data processors and a non-transitory computer-readable storage medium. The non-transitory computer-readable storage medium can contain instructions which, when executed on one or more data processors, cause the one or more data processors to perform a method. The method can include identifying a task to be implemented in the virtual reality environment by the head-mountable display. The method can also include facilitating implementation of the task. Implementation of the task can include displaying a plurality of virtual objects in the display of the VR environment by the head-mountable display.

The method can also include obtaining, during implementation of the task, a set of sensor data from a set of sensors. The method can also include processing the set of sensor data to identify a subset of the virtual objects that the user interacts with using the virtual reality system and a time that each of the subset of virtual objects was interacted with by the user. The method can also include deriving a first performance metric based on the mapped coordinates. The method can also include generating an output based on the first performance metric. The output can quantify a functional visual capability of the user during implementation of the task.

According to certain embodiments, a computer-implemented method is provided. The computer-implemented method can include identifying a task to be implemented in a virtual reality environment. The virtual reality environment can be configured to be displayed in a head-mountable display. The display of the virtual reality environment can include at least one optical setting that is dynamically modified during implementation of the task. The computer-implemented method can also include facilitating implementation of the task. Facilitating implementation of the task can include displaying a plurality of virtual objects in the display of the VR environment by the head-mountable display. The computer-implemented method can also include obtaining a set of sensor data from a set of sensors during implementation of the task.

The computer-implemented method can also include processing the set of sensor data to map a first set of coordinates representing movements in the virtual reality environment directed by the user with a second set of coordinates specifying locations of the dynamic virtual objects in the virtual reality environment. The computer-implemented method can also include deriving a first performance metric based on the mapped coordinates. The computer-implemented method can also include processing the set of sensor data to derive spatial movements of the head-mountable display during implementation of the task. The spatial movements can indicate head movements of the user to interact with the virtual objects during the task. The computer-implemented method can also include deriving a second performance metric based on the derived spatial movements. The computer-implemented method can also include generating an output based on the first performance metric and the second performance metric. The output can quantify the functional visual capability of the user and the spatial movements of the user to interact with the virtual objects during implementation of the task.

Some embodiments of the present disclosure include a system including one or more data processors. In some embodiments, the system includes a non-transitory computer readable storage medium containing instructions which, when executed on the one or more data processors, cause the one or more data processors to perform part or all of one or more methods and/or part or all of one or more processes disclosed herein. Some embodiments of the present disclosure include a computer-program product tangibly embodied in a non-transitory machine-readable storage medium, including instructions configured to cause one or more data processors to perform part or all of one or more methods and/or part or all of one or more processes disclosed herein.

The terms and expressions that have been employed are used as terms of description and not of limitation, and there is no intention in the use of such terms and expressions of excluding any equivalents of the features shown and described or portions thereof. It is recognized, however, that various modifications are possible within the scope of the systems and methods claimed. Thus, it should be understood that, although the present system and methods have been specifically disclosed by examples and optional features, modification and variation of the concepts herein disclosed should be recognized by those skilled in the art, and that such modifications and variations are considered to be within the scope of the systems and methods as defined by the appended claims.

This summary is not intended to identify key or essential features of the claimed subject matter, nor is it intended to be used in isolation to determine the scope of the claimed subject matter. These illustrative examples are mentioned not to limit or define the disclosure, but to provide examples to aid understanding thereof. Additional embodiments and examples are discussed in the Detailed Description, and further description is provided there. The subject matter should be understood by reference to appropriate portions of the entire specification of this disclosure, any or all drawings, and each claim.

The foregoing, together with other features and embodiments will become more apparent upon referring to the following specification, claims, and accompanying drawings.

BRIEF DESCRIPTION OF THE FIGURES

Features, embodiments, and advantages of the present disclosure are better understood when the following Detailed Description is read with reference to the following figures.

DETAILED DESCRIPTION

Figure 1:
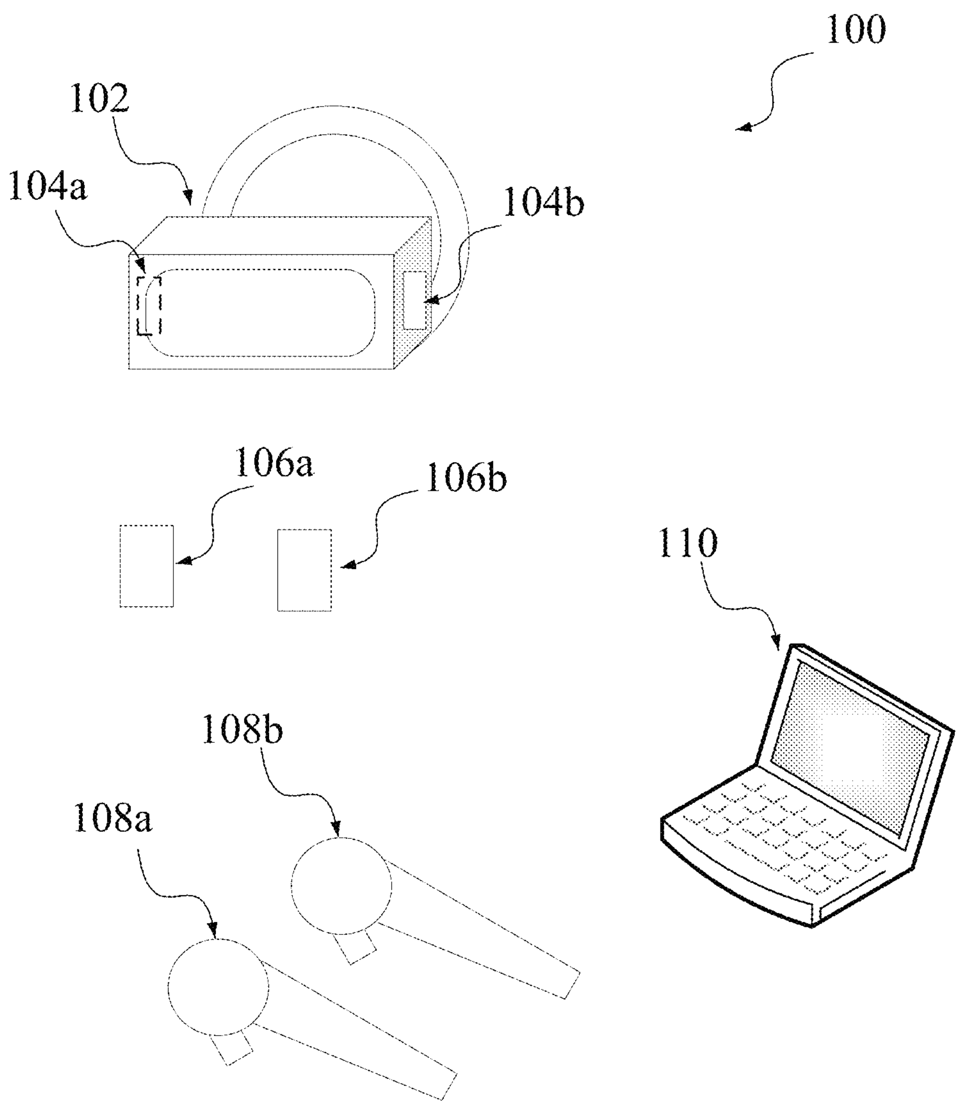
FIG. 1 is a block diagram illustrating components of the virtual environment system.

Techniques disclosed herein relate generally to systems and processes for configuring and using one or more virtual-reality devices to present a task and one or more task environments with varied assessment conditions (e.g., varying light, contrast, color conditions) and to capture a user's interaction with the task environments. An interaction as described herein can include a selection of a virtual object in a virtual reality environment with an interaction type that corresponds to an interaction type for a task. For instance, in an object selection task, the interaction type can include the user moving a position of the user over a position of a virtual object in the virtual reality environment (and optionally providing a triggering action) to interact with the virtual object. The user can interact with a number of virtual objects during the performance of the task.

The system and process can generate a metric characterizing a functional visual capability or visual function of the user based on the interaction, which can be (for example) presented to the user and/or transmitted to another device. The metric can be determined based on how well and/or how quickly a user performs each of one or more tasks and/or user movement or position during a task (e.g., a degree to which a user leans forward) and how the task performance, movement, and/or position vary across assessment conditions.

The systems and processes can thus support rapidly collecting a high volume of multi dimensional measurements within controlled and reproducible testing conditions, such that comparisons across time points can provide controlled and quantifiable information as to how a user's functional visual capabilities are changing. In some instances, such a system can be used as a primary endpoint in clinical studies for testing Investigational Medicinal Products in ophthalmology.

In an exemplary embodiment, the present embodiments can provide systems and methods performed by a virtual environment system. The virtual environment system can include various components, such as a head-mountable display, base stations, and/or hand controllers tracking hand movements of the user. The virtual environment system can also include a computing device capable of performing some or all computational actions described herein. The head-mountable display can include a display configured to present visual stimuli, one or more speakers configured to present audio stimuli, one or more sensors (e.g., one or more accelerometers) configured to measure device movement (corresponding to head movement), one or more cameras configured collect image or video data of a user's eyes (to facilitate tracking eye movements), sound or haptic feedback, and/or one or more speakers configured to capture audio signals. The one or more virtual-reality devices can include one or more sensors that can be worn or attached to a user's hand or arm or include sensors external to the system (e.g., sensors disposed on a chair), which can be used to track hand and/or arm movement.

The virtual environment system can execute one or more tasks. A task can include a set of instructions executed by the virtual environment system. For example, a task can include an object selection task that displays one or more virtual objects in a visual scene and allows for interactions with the virtual objects for a time duration. The task can be selected from multiple task types based on various parameters, such as a specified optical condition related to the user. The task can be executed to display one or more virtual objects in a visual scene.

The virtual reality system can include one or more sensors (e.g., one or more accelerometers and/or cameras) to detect whether, when, and/or how a user is moving his or her head, hands, and/or arms. Measurements from the sensor(s) may be used to infer a position, location, and/or tilt of a user's head, hand and/or arm, respectively. The virtual environment system can translate real-world movement, position, location, and/or tilt into a virtual-environment movement, position, location, and/or tilt, respectively. In some instances, the coordinate system can be the same for the real-world and the virtual-environment data, such that a movement by a given amount in a given direction is the same in either space. However, the virtual-environment space may be configured such that any movement, position, location, and/or tilt associated with the user carries information relative to one or more other objects in the visual scene. For example, in the virtual-environment space, data conveying how a user is moving his or her arm can indicate how the movement changes a relative position between the user's arm and a particular virtual object in the virtual-environment space. This relative information can be used to determine whether and/or how a user is interacting with an object in a virtual space (e.g., whether a user has touched, grabbed, and/or moved a virtual object). Task performance may be determined based on whether and/or when a given type of interaction occurred.

During implementation of the task, a virtual environment optical setting can be dynamically modified (e.g., a modified lighting setting in the visual scene). The display of the virtual reality environment can be modified during implementation of a task. The modified optical setting(s) in the virtual reality environment can allow for a user to interact with virtual objects in the modified optical conditions as provided in the virtual reality environment, which can provide insight into functional visual capabilities of the user.

After completion of one or more tasks, the system can process sensor data obtained during implementation of the task to generate output that characterizes and/or quantifies the functional visual capability of the user. The output can quantify performance metrics relating to virtual objects with which the user interacted and spatial movements of the user during the task.

The present embodiments can provide a virtual reality system that can execute a task and captures sensor data from a series of sensors included in the virtual reality system. The virtual reality system includes a head-mountable display that displays a visual scene with one or more modified optical settings. A virtual reality environment displayed on the head-mountable display can simulate real world environments and can provide an approximation to assess functional visual capabilities of a user. The virtual reality environment can represent the scenes in an enclosed, confined fashion, shielding from external ambient light such that tests can be executed at defined light conditions (e.g., luminosity, color, contrast, and scene composition settings can be controlled in the visual scene).

The virtual environment system can be used anywhere without requiring special facilities/resources. The system can simultaneously measure body posture and changes to the posture as well as hand movements, which can provide insights in user hand-eye coordination and user compensation strategies as a result of visual disability. The system can also measure user performance of activities of daily living as provided in the VR environment that can comprise a measurement of functional vision performance.

Light and scene conditions include any of: luminance (e.g., different light levels from bright to dark and vice versa), dynamic changes of luminance (e.g., flickering light, sudden changes, gradual changes, fading in/out), etc. Scenes can be of low complexity, and real world scenes can be represented by 360 degree panorama images of objects (e.g., restaurants, landscape, night/day scenes, busy road). The simulation of real world scenes can be provided by rendering and computer 3D modelling. The virtual environment system can incorporate any of: eye tracking, hand tracking, body/motion capture to assess and track changes in posture as indicators of users coping/compensation behavior, etc. The system can also include object selection and human-system interactions such as foot-switch, audio processing, voice command, gestures, etc.

As used herein, the term "virtual reality environment" or "VR environment" relates to an electronically-generated display in a VR-enabled device, such as a head-mountable display (HMD) as described herein. The VR environment can display one or more virtual objects that can be static or dynamic (e.g., moving) within the VR environment. In some instances, the environment can incorporate both virtual objects and depictions of real-world features, such as an augmented reality (AR) or extended reality (XR) display. The user can interact with objects in the VR environment using a VR environment system as described herein.

The following examples are provided to introduce certain embodiments. In the following description, for the purposes of explanation, specific details are set forth in order to provide a thorough understanding of examples of the disclosure. However, it will be apparent that various examples may be practiced without these specific details. For example, devices, systems, structures, assemblies, methods, and other components may be shown as components in block diagram form in order not to obscure the examples by unnecessary detail. In other instances, well-known devices, processes, systems, structures, and techniques may be shown without specific details in order to avoid obscuring the examples. The figures and description are not intended to be restrictive. The terms and expressions that have been employed in this disclosure are used as terms of description and not of limitation, and there is no intention in the use of such terms and expressions of excluding any equivalents of the features shown and described or portions thereof. The word "example" is used herein to mean "serving as an example, instance, or illustration." Any embodiment or design described herein as an "example" is not necessarily to be construed as preferred or advantageous over other embodiments or designs.

I. Hardware Overview

FIG. 1 is a block diagram illustrating components of the virtual environment system 100. The system can include any of a head-mountable display 102, eye tracking sensors 104*a-b*, base 106*a-b* stations, hand controllers 108*a-b*, and a computing device 110.

The head-mountable display (HMD) 102 can provide a controlled and self-contained environment while being worn by the user (i.e., controlled light conditions, contrast, scene settings during execution). The HMD 102 can prevent ambient light from the real environment from interfering with the VR scene and subsequently allows to alter such conditions in a defined and controlled manner. In some embodiments, the capability of projecting a scene via the HMD display can be integrated in the head-mounted-display device. In some embodiments, the system may make use of an external device (e.g., handheld device/smartphone) mounted in a special case (e.g., cardboard) forming a head-mounted-display.

The HMD 102 can be equipped with a set of electronic sensors, such as rotational velocity sensors, eye tracking sensors 104*a-b*, and a camera. The sensors of the HMD 102 can record the spatio-temporal dynamics of head movements, such as rotational velocity, translational movements and, in conjunction with the base stations, reconstruct 3D positional information (in time and space). The eye tracking sensors 104*a-b* can allow for eye tracking and can capture sensor data about the eye, such as blinks, pupil size, gaze direction, saccades, as well as corresponding timestamps. Subsequent analyses of such recorded sensor data can allow for the assessment of spatio-temporal reactions and behavior (head and eyes) of the user in relation to changes of luminance, contrast, scene and object properties.

Base stations 106*a-b* can be equipped with opto-electronic sensors to detect and reconstruct positional information of HMD 102 and hand controllers 108*a-b*. The base stations 106*a-b* can reconstruct positional information from the HMD 102 and hand controllers 108*a-b* in time and space. This can allow for the analysis of the influence of light and scene conditions as provided on the HMD 102 of the test person's performance, movement, and traces in space and time of the hand and head trajectories. In some instances, the HMD 102 can perform functionalities described with respect to the base stations 106*a-b*.

Hand controllers 108*a-b* can be equipped with electronic sensors, such as accelerometers and tags which allow the reconstruction of 3D positional information. The sensors can record the spatio-temporal dynamics of movements of both hands, and, in conjunction with the base stations, derive 3D positional information at any time during the use of the system. Subsequent analyses of such recorded sensor data can allow for assessing spatio-temporal reactions and behaviors of the user in relation to changes to the VR environment projected to the HMD 102. The system tracking both hand motion (e.g., via hand controllers 108*a-b*) and eye motion (e.g., via HMD 102) can track functional visual capability, light conditions, and behavior (and subsequently performance) when performing one or more tasks.

A motion tracking system can track multiple degrees of freedom of motion (position and orientation) of the display, as well as user body landmarks of interest (e.g., hands, trunk location). The motion tracking system can be (for example) inside-out (e.g., fusion of an optical sensor with depth sensors, Light Detection and Ranging (LiDAR), inertial measurement units, magnetometers), etc. The motion tracking system can track the position and/or orientation and the position of points of interest from other body parts (e.g., hands, arms). The motion tracking system can include additional components where a single device or a set of external devices (optical-based, infrared-based, depth-based, ultra-wide band systems) can track the position of landmarks on the user and environment of use directly (e.g., through visual features) or through additional body-mounted, handheld, or environment-placed active (e.g., photodiodes, IMU, magnetic sensor, UWB receiver) or passive (e.g., reflective markers) tracking devices.

The computing device 110 (e.g., a personal computer (PC), laptop) can run at least a portion of the controlling software of the VR system (management & projection of scenes, communication with the HMD, controllers, base stations). The computing device 110 can provide functionality to (for example) register and manage user data, to edit and/or select configuration parameters. The computing device 110 can also or alternatively manage the recorded data (e.g., data representing head movements, eye movements, pupil dilations) and user data and manage the secure data transfer to another data infrastructure. The computing device 110 can include a processing unit to execute the commands defined in the software program and handle the communication with the display and optional feedback systems available (e.g., audio, haptic).

In some embodiments, the system can include any of a set of handheld controllers, a motion tracking system, an eye tracking system, auditory system, haptic feedback system, and an auditory input system.

The computing device 110 can include software for controlling the nature of the visual scene projected in the HMD 102, providing functionality to capture and record user actions/interactions and manage recorded sensor data as well as user data (e.g., user height, length of arms, user identifier). The software and its configuration can control the VR scene and present an environment as described herein. The software can control a projection of a visual scene in relation to the user's field of view. The software can convert user interactions with the visual scene into actions and progression of a task (e.g., proceed to the next stage). The software program can also handle the data logging of the available tracking data and meta information.

The software can include a module for a supervising user to select one or more tasks for implementation of the task for a user. The software can include a module for the supervising user to register a user and enter demographic data (e.g., age), body parameters (e.g., arm length, height), eye parameters (e.g., interpupillary distance), etc. The software can also include a module for the supervising user to set up the system according to individual physical parameters (e.g., eye tracking calibration, arm reach, seated body height).

The software can include functionality to edit and/or select a predefined system configuration. The configuration can define assessment parameters, such as light conditions, timing and duration of task and subtasks, contrast of scene objects, size of scene object, an object velocity, a target object distribution, and/or makeup of scene objects. The software can configure the visual scene (panorama scenes) setting, such as a basic scene with no decorations, a city night scene, a hotel lobby, and/or a forest. The software can also include functionality to store (configuration, user, sensor recording) and to transfer data in a secure manner to another infrastructure for further processing and analyses.

The software can execute tasks for the assessment of visual function. A task can comprise displaying a virtual reality environment with a requested action to be performed by the user interacting with the virtual reality system. For example, a task can relate to an object selection task. The object selection task can include displaying a scene of a plurality of objects and requesting the user to identify objects in the scene (e.g., by visual discrimination of the visual scene or reading a text prompt) of an object type. For example, this can include identifying a food item (e.g., an apple) in a scene comprising a table and a plurality of virtual objects of varying types.

The tasks can include an objective to measure user performance in selecting abstract objects or renderings of real world objects (e.g., cups, plates, keys). For instance, a task can include an object/obstacle interaction task with the objective to measure users' performance in recognizing, reacting to (e.g., selecting a moving object), and avoiding moving abstract objects (e.g., moving spheres). Multiple differing types of tasks can be implemented in the virtual reality environment. For example, a task can be selected for implementation based on a visual condition of a user, selected as part of a pre-defined order, randomly selected, etc.

II. Execution of a Selected Task in a Visual Scene

Figure 2:
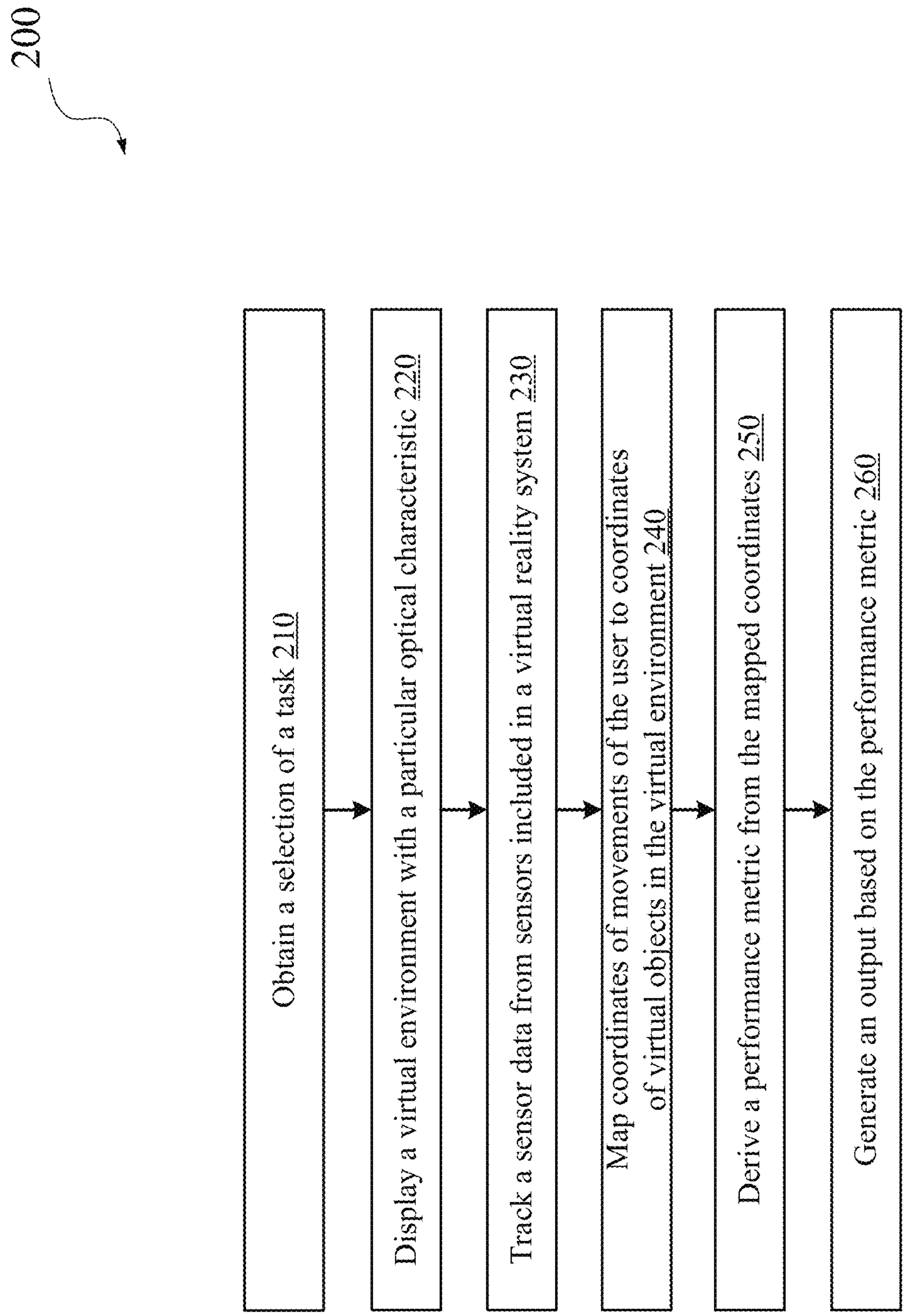
FIG. 2 is a flow process illustrating an example method for executing a selected task in a virtual environment.

FIG. 2 shows a flow process 200 illustrating an example method for executing a selected task in a visual scene. As described herein, multiple types of tasks can be implemented using the virtual reality system. For example, a task can include an object selection task, an object interaction task, and/or a reading task as described herein. In some instances, a series of tasks can be implemented in an order (e.g., in a random order, in an order defined by user input).

As described above, the task can include displaying a scene in the virtual reality display and requesting an action to be performed in the virtual reality environment. In some instances, a series of tasks can be configured to be implemented according to an order, where after completion of a first task of the series of tasks, a second task can be initiated (e.g., a new scene can be displayed at the virtual reality display and a new requested action to be performed can be provided).

At block 210, the system can obtain a selection of a task. This can include identifying a selection to initiate a task or a series of tasks according to an order. For example, the task can be selected based on an input provided by a user (or a supervising user) based on a visual condition related to the user.

At block 220, a visual scene can be displayed with a particular visual characteristic. A particular optical characteristic can include any feature of the virtual reality display. Examples of the particular optical characteristic can include a light level, a contrast of the virtual objects in the display, an addition of a text label, a number/size/location of virtual objects in the display, a trajectory of movement of the virtual objects in the display, etc.

The visual scene can display one or more virtual objects such that the user can interact with them (e.g., by identifying a virtual object, crushing a virtual object moving towards the user). The visual scene displayed can be specific to the selected task.

One or more particular optical characteristics can be dynamically modified during implementation of the task. For example, a dynamically modified particular optical characteristic can include a modified size of the virtual objects (e.g., to make the objects smaller, to modify a text label) during implementation of the task. As another example, a dynamically modified particular optical characteristic can include lowering the light level of the virtual reality display during implementation of the task.

The modified optical characteristics during the task can allow for interaction with virtual objects in the virtual reality environment to test functional visual capabilities of a user in modified optical conditions. For example, as a light level is lowered during implementation of the task, the performance of the user during the task (e.g., a performance in identifying virtual objects) can change, which can further identify functional visual capabilities of a user.

At block 230, sensor data can be obtained from a series of sensors included in the virtual reality system. The sensor data can be obtained from sensors in the system (e.g., set of eye sensors, a set of base stations, a set of hand controllers). The sensor data obtained from the series of sensors can be arranged by data type for subsequent processing. For example, data from eye sensors and data from hand controllers can be arranged separately by a timestamp of the sensor data for subsequent processing.

The obtained sensor data can be processed to derive characteristics of the user's behavior in the virtual reality environment. For example, data from eye tracking sensors can capture pupil locations over time, which can be mapped to real-world coordinates.

Changes in the identified coordinates in the real-world coordinate space over time can be identified, specifying movements of the object (e.g., the pupil) over time. For example, a change in identified coordinates of a pupil over a time duration can specify a movement of the pupil over that time duration. As another example, a change in identified coordinates of a head (as provided by base station sensor data) in the real-world coordinate space can provide a movement of the head of the user.

As described in greater detail below, the spatial movements can be tracked during the task using the sensor data. Spatial movements can include detected physical movements of the head-mountable display as captured by base station sensors. For example, a user may move the head to perform the requested action associated with the task to compensate for various visual limitations of the user. The set of spatial movements can also identify posture changes, head movements, sudden movements, pupil size, eye movements of a user etc. The spatial movements can be identified in a second performance metric that can be provided in the output as described below.

In some instances, the set of spatial movements can specify user movements, blinking, pupil size of a user, etc. Such movements may include anomalous actions that deviate from an expected range of spatial movements during an implementation of the task. The anomalous movements or actions detected by the virtual reality system can be provided as part of the output.

The identified coordinates of an object in a real-world coordinate space can be mapped to coordinates in the virtual reality environment. For example, coordinates specifying pupil location in the real-world coordinate space of the user at a first time instance can be mapped to specify a direction of the pupil in the virtual reality environment coordinate space. The mapped coordinates of objects in the virtual reality environment can be used to identify whether a user interacts with a virtual object, as noted below.

At block 240, coordinates of movements of the user can be mapped to coordinates of virtual objects in the visual scene. The measured coordinates of the user (e.g., a pupil, hand, head of the user) in the virtual reality environment can be compared with coordinates of virtual objects in the virtual reality environment to determine whether a user has interacted with a virtual object in a particular manner in the visual scene. For example, it can be determined that a user interacted with a virtual object in a particular manner if coordinates of an object in the visual scene are within a threshold proximity from coordinates of the user's hand in the visual scene at a given time point.

In some instances, determining that a user has interacted with a virtual object in a particular manner can include detecting that a mapped virtual-space location of a user's hand corresponds to a virtual-space location of a virtual object as well as detecting a trigger. A trigger event can include interaction with a trigger button on the hand controllers, an audible trigger word detected by the virtual reality system, detecting gaze towards a virtual object for a specified amount of time, etc. For instance, a criterion may be configured to be satisfied if the virtual-space location of a hand of a user is within a threshold proximity of a location of the virtual object and if the trigger was detected within a threshold time from the virtual-space location of the hand being within the threshold proximity of the location of the virtual object.

At block 250, a performance metric can be derived from the mapped coordinates. The performance metric can quantify a performance of a user of the specified task. For example, if the selected task is an object selection task, the performance metric can quantify a number of virtual objects correctly identified by the user and a time of identifying/selecting each virtual object. In some embodiments, the performance metric can indicate or can be based on a number of virtual objects with which the user interacted in a particular manner (e.g., selecting a virtual object of a correct object type or trajectory), a number of virtual objects with which the user interacted in another particular manner (e.g., selecting a virtual object of an incorrect object type or incorrect trajectory), a virtual-space location of each of one or more virtual objects with which the user interacted in a particular manner (e.g., relative to a virtual-space location of the user and/or of an object of a target type), etc. The performance metric can be indicative of functional visual capabilities of the user. In some instances, block 250 includes deriving a performance metric for each of multiple optical settings.

In deriving a performance metric, the number of virtual objects with which the user interacted according to the task can be identified. The performance metric can include a value or series of values specifying the number of virtual objects with which the user interacted during the task. For example, the performance metric can include a value based on a number of virtual objects interacted with by the user, where a greater number of virtual objects interacted with by the user increases the value of the performance metric.

In some embodiments, the performance metric can provide insights into a differing performance of the user in completion of the task with dynamically modified optical characteristic(s) in the visual scene. For example, as the light level of the visual scene decreases during implementation of a task, the measured performance of the user in identifying virtual objects can decrease. As another example, it can be determined if a performance of a user with regards to selecting or interacting with virtual objects in accordance with a task decreases as the light level of the visual scene decreases. The performance metric can identify that the performance of the user (e.g., the number of virtual objects correctly identified by the user) declined as the light level of the virtual reality environment decreased.

In some embodiments, a second performance metric can be derived based on the spatial movements of the user during the task. The second performance metric can be used with the first performance metric to generate multiple datasets as represented in the output.

The set of sensor data (e.g., data obtained from eye tracking sensors 104*a-b*, hand controllers 108*a-b*, base station sensors 106*a-b*) can be processed to derive spatial movements of the head-mountable display during implementation of the task. Spatial movements can indicate head movements of the user when interacting with the virtual objects. Such spatial movements can further quantify functional visual capabilities of the user, as more spatial movements may generally represent an increased level of effort needed to correctly identify virtual objects. For example, if a user has limited peripheral vision, the user may move their head to identify objects in the visual scene to compensate for the limited peripheral vision. The detected spatial movements can quantify such a limitation that can be represented in an output, as described below.

The second performance metric can be generated based on the derived spatial movements. The second performance metric can include a value quantifying a number and magnitude of spatial movements during the task, quantifying head movements by the user while performing the task. The output can be updated to represent both the first performance metric and the second performance metric. The output can quantify the functional visual capability of the user and the spatial movements of the user to interact with the virtual objects in the virtual reality environment.

At block 260, an output can be generated. The output can provide a representation of the performance of a user during implementation of the task and/or the spatial movements of the user during implementation of the task. For example, the performance metric can include a series of values indicative of virtual objects with which the user interacted during implementation of the task. The system can graphically represent the performance metric in the output, providing a visual representation of the virtual objects in which the user interacted during implementation of the task. The output can be analyzed to assist in identifying various optical conditions of the user. The output is discussed in greater detail with respect to FIG. 5.

Figure 3:
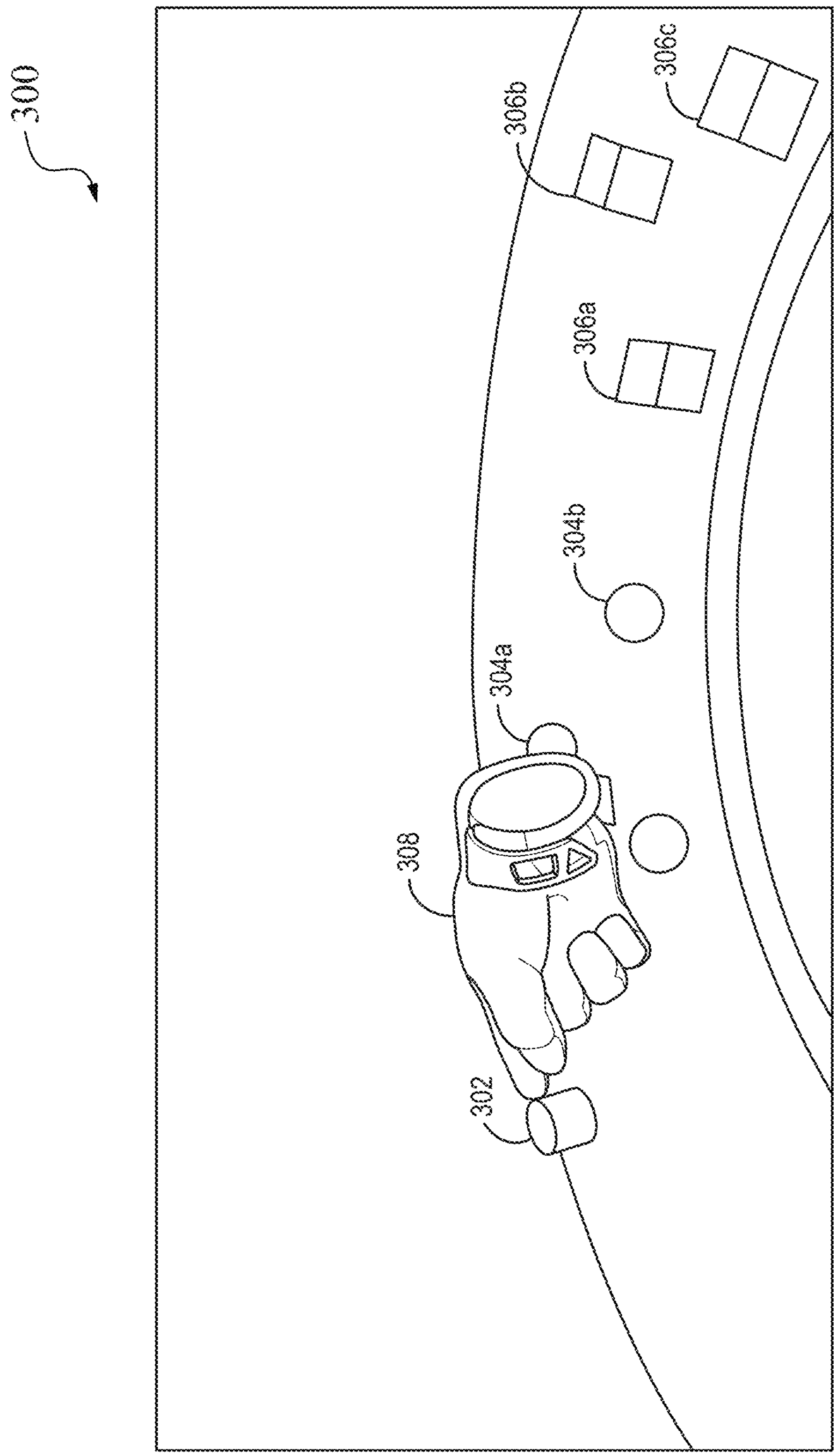
FIG. 3 illustrates an example virtual environment display of an object selection task.

FIG. 3 illustrates an example of the virtual environment display 300 of an object selection task. For example, in FIG. 3, a number of virtual objects can be depicted in the virtual environment display. For example, the visual scene can include virtual objects of a first type 302, virtual objects of a second type 304*a-b*, and virtual objects of a third type 306*a-c*. The user can interact with virtual objects in the visual scene by identifying a virtual object in a scene of objects. For instance, a position of the user 308 can be provided in the virtual environment display 300 and the display 300 can be modified based on detected movements by the user. Further, the user can select a virtual object by directing a position of the user over a virtual object and providing a trigger (e.g., pressing a button on a hand controller). In some embodiments, haptic stimuli can be displayed responsive to selection of an object as feedback. For instance, a sound stimuli can be provided based on a correct or incorrect selection of an object.

As shown in FIG. 3, the task can include an object selection task. The objective (or requested action) of the object selection task can be to select an abstract target object in a defined number of distractor objects spread in a defined manner on a virtual table. In some instances, the object selection task can specify various object types to locate and select within a scene of objects. For example, in a scene comprising a table with various object types (e.g., food items, personal items, random objects), the virtual reality system can prompt for selection of a first object type (e.g., prompt to identify an apple located on the table). Accordingly, in this example, the number of objects that the user interacts with can comprise objects of an object type prompted for selection during the object selection task.

The number of objects, the nature of the objects, the contrast of objects, light conditions, timing, duration of each task and each trial, the spread of objects, object shapes, object content (e.g., whether the object is filled with text), and the geometry of the table can be configurable. Various measurements can be obtained, such as the object selection performance (e.g., both correctly selected and incorrectly selected), time of selection of each object, gaze direction, head position and movement, hands position, movement and velocity, upper body posture, and eye parameters (pupil size over time, fixation, saccades). The outcome of the task can be the performance as a function of light and contrast conditions as an indicator of visual functioning suited to differentiate users with and without any limits to functional visual capabilities, assess disease state and progression, and assess treatment outcome.

In some embodiments, characteristics of the task can be modified based on a performance of the user during execution of the task. For example, a difficulty of the task (e.g., the number of objects in the environment, a speed of moving objects in the environment, light settings) can be increased or decreased based on a performance of the user during the task.

Figure 4:
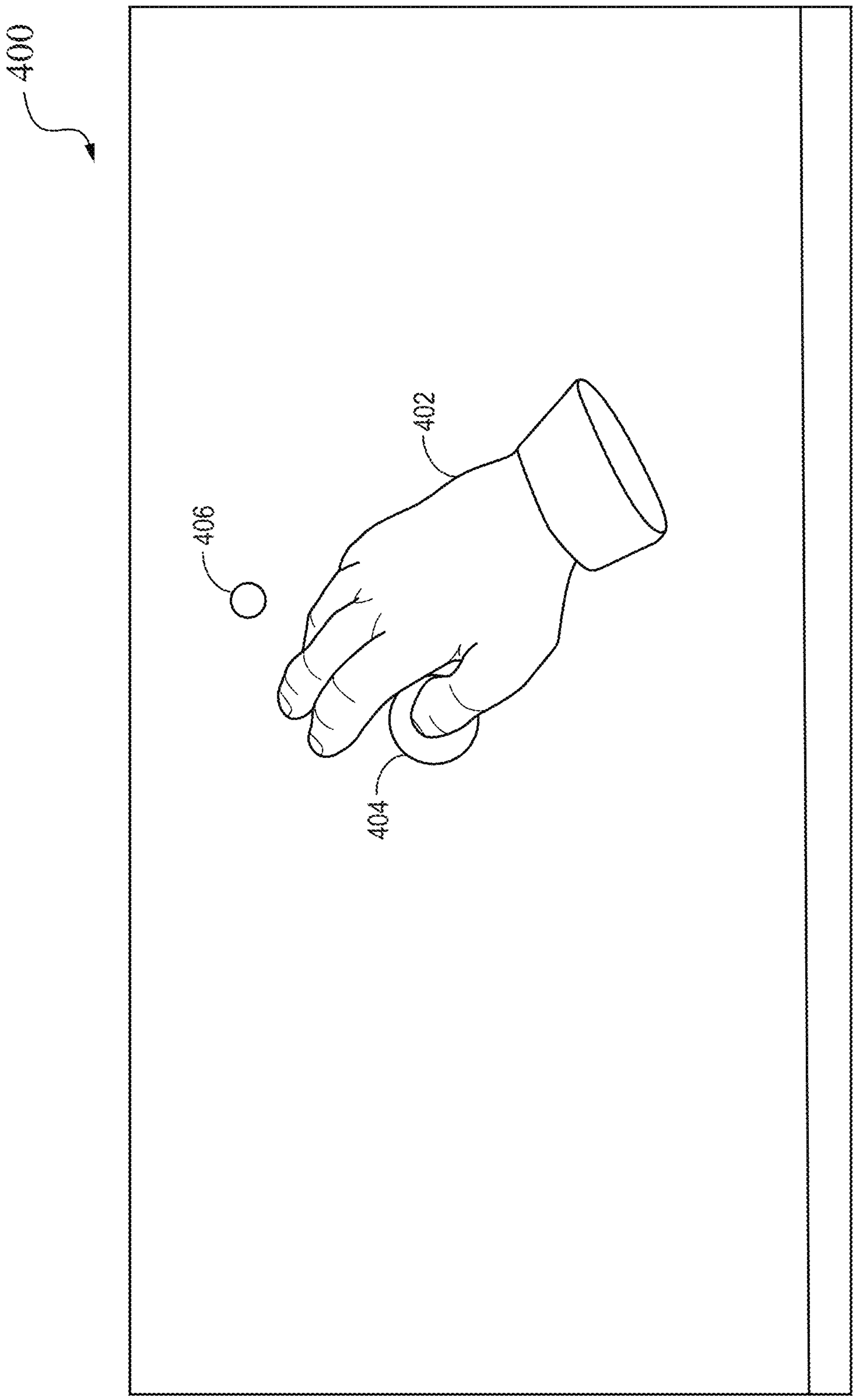
FIG. 4 illustrates an example virtual environment display of an object interaction task.

FIG. 4 illustrates an example of the virtual environment display 400 of an object interaction task. The objective of the object interaction task can be to recognize moving virtual objects 404, 406 and to avoid collision with such objects. Avoiding collision with virtual objects moving towards the position of the user can include selecting the virtual objects (e.g., to "crush" the virtual objects using hand controllers). In some instances, the movements of the user can be to avoid incoming virtual objects.

During implementation of the task, the user interacting with a head-mountable display can move their eyes/head to move a virtual position of the user 402 in the visual scene to select incoming objects (e.g., select virtual object 404 to crush it). Any of a number of virtual objects, a nature of the objects, a contrast of the objects, light conditions, a speed of the objects, a location where the objects are created, a direction and location where objects will pass to the user (e.g., via the HMD), and a timing and duration of the task and each trial of the task.

Measurements capable of being captured during this task can include a performance as reflected by a number of selected objects (touched, missed, ignored), a time to selection, a scene hemisphere where objects were selected/missed, a gaze direction, a head position and movement, a hand position, movement, and velocity, an upper body posture, and eye parameters (pupil size over time, fixation, saccades). The output of the task can be the performance as a function of light, contrast, and/or object conditions as an indicator of visual functioning suited to differentiate users with and without any limits to functional visual capabilities, assess disease state and progression, and assess treatment outcome.

In some embodiments, the task can include a reading-based task. The reading-based task can include a request to perform a corresponding action based on text displayed on the virtual reality environment. For example, a reading-based task can include displaying a scene comprising text elements (e.g., a bus stop sign indicating bus scheduling). In this task, the user interacting with the virtual reality system is asked to identify a bus that is indicated in the sign, for example. Aspects of the reading-based task can be incorporated into any other task as described herein.

In some embodiments, a task can include a calibration task. The calibration task can include presenting a visual scene and modifying aspects of the scene to increase a quality of obtained data, control of the system, etc. For example, virtual objects can be modified during the calibration task to calibrate aspects of the task. Calibration can consist in the implementation of a standard assessment of visual function. Calibration can also include identifying features of the user, such as a height of the user, where the task can be adapted based on the features of the user.

III. Output Generation

Figure 5:
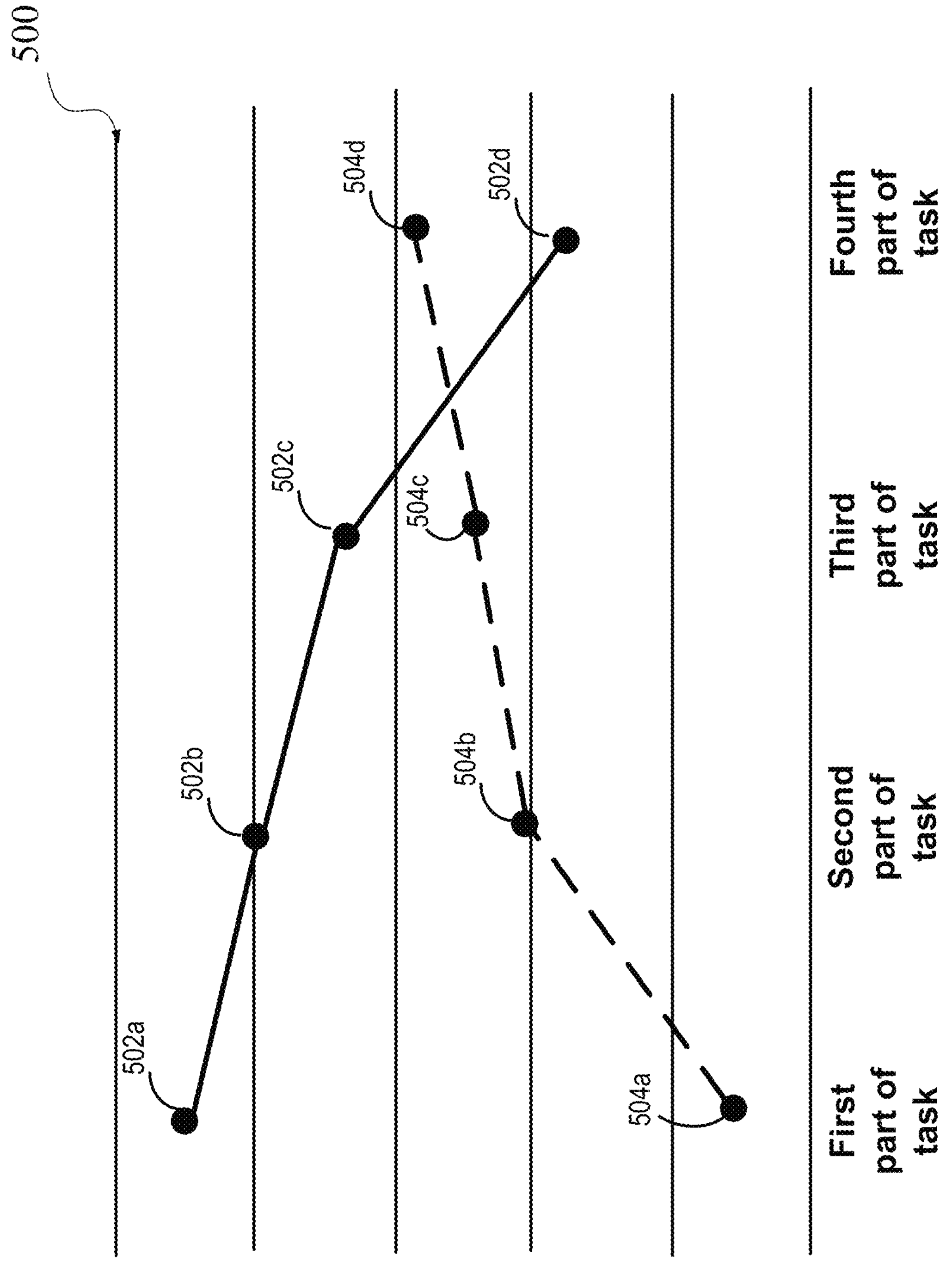
FIG. 5 illustrates an example output representing a performance of a user during a task.

FIG. 5 illustrates an example output 500 representing a performance of a user during a task. As shown in FIG. 5, the output can quantify the performance of a user during implementation of the task. The output can be based on the derived performance metric(s) as described herein.

In the example as illustrated in FIG. 5, the output 500 can quantify a number of virtual objects in which the user interacts during each part of performance of the task. The output can be generated based on a performance metric specifying a performance of the user during each part of the task. Each point (e.g., 502*a-d*) illustrating a first trend line (e.g., the full line) can include a number of objects in which the user interacts during parts of the task, as represented in a first performance metric. The output can quantify a performance of the user during implementation of the task, which can be analyzed to identify various functional visual capabilities of the user.

The output can also illustrate various spatial movements of the user during implementation of the task. The second performance metric as described herein can specify a number/magnitude of spatial movements in performance of the task during the parts of the task. Each point 504*a-d* illustrating a second trend line (e.g., the dashed line) can quantify the spatial movements of the user during performance of portions of the task, as specified in the second performance metric.

For example, increased spatial movements can indicate that the user has an increased effort in identifying virtual objects in the visual scene in low light conditions. The output incorporating the second performance metric can provide an illustration of spatial movements during implementation of the task that can be indicative of the strain of the user in performing the task.

In some instances, the set of sensor data can capture various movements or actions performed by the user, such as a sudden movement, eye blinks, changes in pupil size, etc. Many of such actions can be anomalous (e.g., of a type or magnitude that deviates from an expected series of actions) in nature and can be indicative of various visual limitations of the user. The output can specify an action type and a time of occurrence of anomalous events detected during implementation of the task.

In some embodiments, the output can provide a graphical representation of regions in the visual scene in which there was an interaction with virtual objects while executing the task. For example, the graphical representation can provide a heatmap identifying regions (e.g., quadrants) of the visual scene that include locations of virtual objects. The heatmap can provide insights into regions in which virtual objects were identified by the user and corresponding regions in which vision of the user have various functional visual capabilities.

IV. Computing Environment

Figure 6:
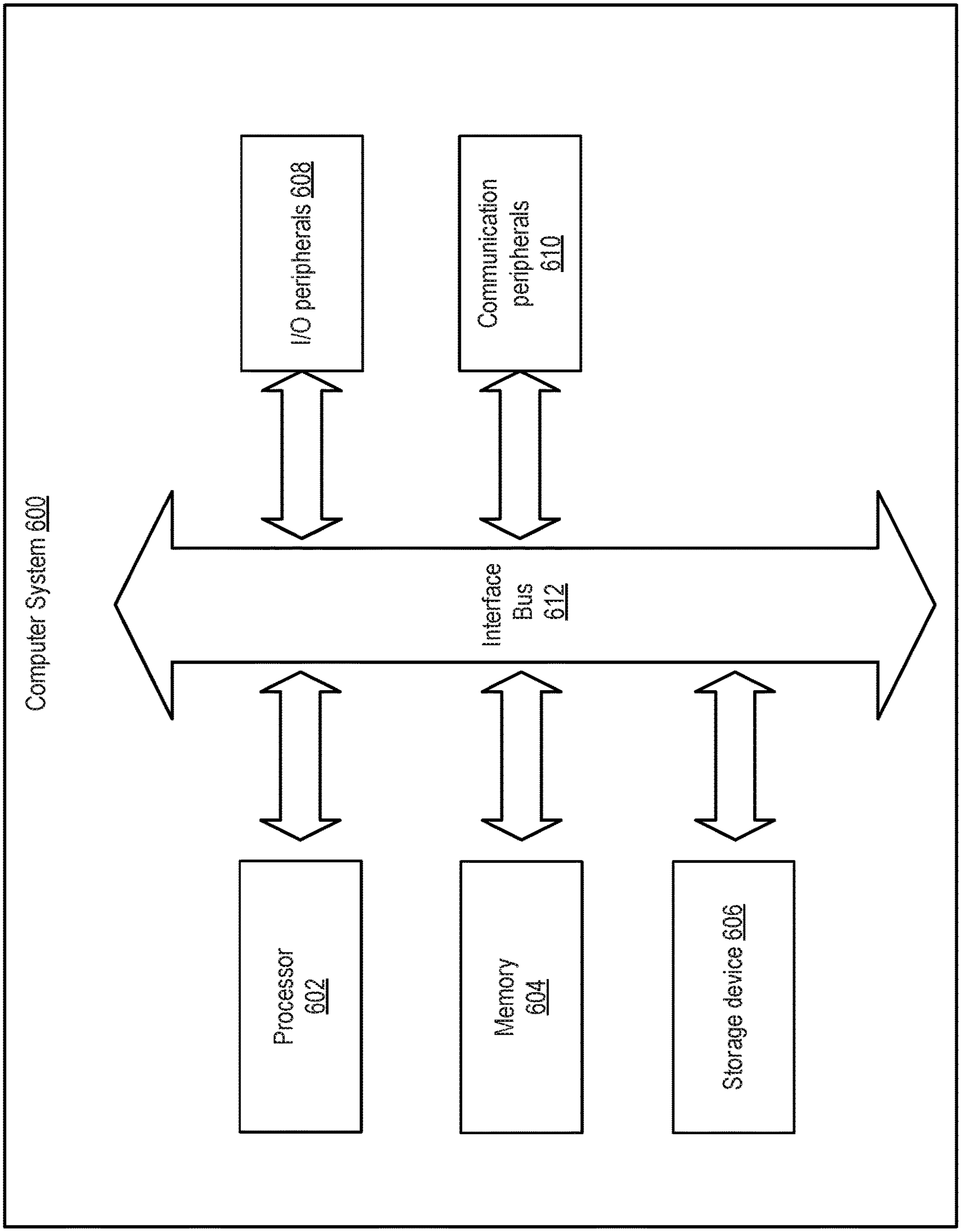
FIG. 6 illustrates an example of a computer system for implementing some of the embodiments disclosed herein.

FIG. 6 illustrates an example of a computer system 600 for implementing some of the embodiments disclosed herein. Computer system 600 may have a distributed architecture, where some of the components (e.g., memory and processor) are part of an end user device and some other similar components (e.g., memory and processor) are part of a computer server. Computer system 600 includes at least a processor 602, a memory 604, a storage device 606, input/output (I/O) peripherals 608, communication peripherals 610, and an interface bus 612. Interface bus 612 is configured to communicate, transmit, and transfer data, controls, and commands among the various components of computer system 600. Processor 602 may include one or more processing units, such as CPUs, GPUs, TPUs, systolic arrays, or SIMD processors. Memory 604 and storage device 606 include computer-readable storage media, such as RAM, ROM, electrically erasable programmable read-only memory (EEPROM), hard drives, CD-ROMs, optical storage devices, magnetic storage devices, electronic non-volatile computer storage, for example, flash memory, and other tangible storage media. Any of such computer-readable storage media can be configured to store instructions or program codes embodying aspects of the disclosure. Memory 604 and storage device 606 also include computer-readable signal media. A computer-readable signal medium includes a propagated data signal with computer-readable program code embodied therein. Such a propagated signal takes any of a variety of forms including, but not limited to, electromagnetic, optical, or any combination thereof. A computer-readable signal medium includes any computer-readable medium that is not a computer-readable storage medium and that can communicate, propagate, or transport a program for use in connection with computer system 600.

Further, memory 604 includes an operating system, programs, and applications. Processor 602 is configured to execute the stored instructions and includes, for example, a logical processing unit, a microprocessor, a digital signal processor, and other processors. Memory 604 and/or processor 602 can be virtualized and can be hosted within another computing system of, for example, a cloud network or a data center. I/O peripherals 608 include user interfaces, such as a keyboard, screen (e.g., a touch screen), microphone, speaker, other input/output devices, and computing components, such as graphical processing units, serial ports, parallel ports, universal serial buses, and other input/output peripherals. I/O peripherals 608 are connected to processor 602 through any of the ports coupled to interface bus 612. Communication peripherals 610 are configured to facilitate communication between computer system 600 and other computing devices over a communications network and include, for example, a network interface controller, modem, wireless and wired interface cards, antenna, and other communication peripherals.

While the present subject matter has been described in detail with respect to specific embodiments thereof, it will be appreciated that those skilled in the art, upon attaining an understanding of the foregoing may readily produce alterations to, variations of, and equivalents to such embodiments. Accordingly, it should be understood that the present disclosure has been presented for purposes of example rather than limitation, and does not preclude inclusion of such modifications, variations, and/or additions to the present subject matter as would be readily apparent to one of ordinary skill in the art. Indeed, the methods and systems described herein may be embodied in a variety of other forms; furthermore, various omissions, substitutions and changes in the form of the methods and systems described herein may be made without departing from the spirit of the present disclosure. The accompanying claims and their equivalents are intended to cover such forms or modifications as would fall within the scope and spirit of the present disclosure.

Unless specifically stated otherwise, it is appreciated that throughout this specification discussions utilizing terms such as "processing," "computing," "calculating," "determining," and "identifying" or the like refer to actions or processes of a computing device, such as one or more computers or a similar electronic computing device or devices, that manipulate or transform data represented as physical electronic or magnetic quantities within memories, registers, or other information storage devices, transmission devices, or display devices of the computing platform.

The system or systems discussed herein are not limited to any particular hardware architecture or configuration. A computing device can include any suitable arrangement of components that provide a result conditioned on one or more inputs. Suitable computing devices include multipurpose microprocessor-based computing systems accessing stored software that programs or configures the computing system from a general purpose computing apparatus to a specialized computing apparatus implementing one or more embodiments of the present subject matter. Any suitable programming, scripting, or other type of language or combinations of languages may be used to implement the teachings contained herein in software to be used in programming or configuring a computing device.

Embodiments of the methods disclosed herein may be performed in the operation of such computing devices. The order of the blocks presented in the examples above can be varied—for example, blocks can be re-ordered, combined, and/or broken into sub-blocks. Certain blocks or processes can be performed in parallel.

Conditional language used herein, such as, among others, "can," "could," "might," "may," "e.g.," and the like, unless specifically stated otherwise, or otherwise understood within the context as used, is generally intended to convey that certain examples include, while other examples do not include, certain features, elements, and/or steps. Thus, such conditional language is not generally intended to imply that features, elements and/or steps are in any way required for one or more examples or that one or more examples necessarily include logic for deciding, with or without author input or prompting, whether these features, elements and/or steps are included or are to be performed in any particular example.

The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. The use of "adapted to" or "configured to" herein is meant as open and inclusive language that does not foreclose devices adapted to or configured to perform additional tasks or steps. Additionally, the use of "based on" is meant to be open and inclusive, in that a process, step, calculation, or other action "based on" one or more recited conditions or values may, in practice, be based on additional conditions or values beyond those recited. Similarly, the use of "based at least in part on" is meant to be open and inclusive, in that a process, step, calculation, or other action "based at least in part on" one or more recited conditions or values may, in practice, be based on additional conditions or values beyond those recited. Headings, lists, and numbering included herein are for ease of explanation only and are not meant to be limiting.

The various features and processes described above may be used independently of one another, or may be combined in various ways. All possible combinations and sub-combinations are intended to fall within the scope of the present disclosure. In addition, certain method or process blocks may be omitted in some implementations. The methods and processes described herein are also not limited to any particular sequence, and the blocks or states relating thereto can be performed in other sequences that are appropriate. For example, described blocks or states may be performed in an order other than that specifically disclosed, or multiple blocks or states may be combined in a single block or state. The example blocks or states may be performed in serial, in parallel, or in some other manner. Blocks or states may be added to or removed from the disclosed examples. Similarly, the example systems and components described herein may be configured differently than described. For example, elements may be added to, removed from, or rearranged compared to the disclosed examples.

What is claimed is:

1. A method comprising:

identifying a task to be executed in a virtual reality environment, the virtual reality environment is displayed by a head-mountable display, and where display of the virtual reality environment includes at least one optical setting that is dynamically modified during execution of the task;

facilitating execution of the task, wherein execution of the task includes displaying a plurality of virtual objects in the display of the virtual reality environment by the head-mountable display;

obtaining, during execution of the task, a set of sensor data from a set of sensors associated with a user;

processing the set of sensor data to map a first set of coordinates in the virtual reality environment representing movements directed by the user with a second set of coordinates specifying locations of the plurality of virtual objects in the virtual reality environment;

deriving a first performance metric based on the mapped coordinates;

dynamically adapting a task parameter or the at least one optical setting based on the first performance metric during continued execution of the task;

obtaining, during continued execution of the task, a second set of sensor data from the set of sensors;

processing the second set of sensor data to map a third set of coordinates in the virtual reality environment representing movements directed by the user with a fourth set of coordinates specifying locations of the plurality of virtual objects in the virtual reality environment;

deriving a second performance metric based on the mapped coordinates; and generating an output based on the first and second performance metric, the output representing a functional visual capability of the user with dynamically modified optical settings in the virtual reality environment.

2. The method of claim 1, wherein the at least one optical setting is dynamically modified from a first setting to a second setting during the execution of the task, the at least one optical setting including a light intensity setting, a virtual object contrast setting, and a dynamically-modified luminance setting, a number of the plurality of virtual objects displayed in the virtual reality environment, a trajectory of movement of the plurality of virtual objects displayed in the virtual reality environment, and/or locations of the plurality of virtual objects in the virtual reality environment.

3. The method of claim 1, wherein the first performance metric specifies a performance of the user during each part of the execution of the task, wherein the second performance metric specifies a number and/or magnitude of the movements during each part of the execution of the task, wherein the at least one optical setting is dynamically modified to generate different sub-settings, and wherein each part of the execution of the task corresponds to a different sub-setting.

4. The method of claim 1, wherein the set of sensors include: eye tracking sensors disposed in the head-mountable display and configured to track eye movements of the user;

base station sensors disposed in the head-mountable display and configured to identify spatial movements of the head-mountable display; and hand controller sensors configured to track hand movements of the user and/or a triggering event.

5. The method of claim 1, wherein the task is identified from a set of tasks, each task of the set of tasks relates to a particular optical condition relating to the user.

6. The method of claim 1, wherein the task comprises an object selection task, and wherein the object selection task maps movements by the user in the virtual reality environment to locations comprising virtual objects to identify each of the plurality of virtual objects.

7. The method of claim 1, wherein the task comprises an object interaction task, and wherein the object interaction task maps movements by the user in the virtual reality environment to select a location of virtual objects moving toward a position of the user in the virtual reality environment.

8. A virtual environment system comprising:

a head-mountable display configured to display a virtual reality environment; and a computing device comprising:

one or more data processors; and a non-transitory computer-readable storage medium containing instructions which, when executed on the one or more data processors, cause the one or more data processors to perform a method comprising:

identifying a task to be executed in the virtual reality environment by the head-mountable display, and where display of the virtual reality environment includes at least one optical setting that is dynamically modified during execution of the task;

facilitating execution of the task, wherein execution of the task includes displaying a plurality of virtual objects in the display of the virtual reality environment by the head-mountable display;

obtaining, during execution of the task, a set of sensor data from a set of sensors associated with a user;

processing the set of sensor data to identify a subset of the plurality of virtual objects interacted with by a user and a time of interacting with each of the subset of the plurality of virtual objects;

processing the set of sensor data to derive spatial movements of the head-mountable display, wherein the spatial movements are indicative of head movements of the user when interacting with the plurality of virtual objects;

deriving a first performance metric based on the subset of the plurality of virtual objects interacted with by the user and the time of interacting with each of the subset of the plurality of virtual objects and a second performance metric based on the derived spatial movements; and generating an output based on the first and second performance metric, the output representing a functional visual capability of the user with dynamically modified optical settings in the virtual reality environment.

9. The virtual environment system of claim 8, wherein processing the set of sensor data to identify the subset of the virtual objects interacted with by the user further comprises:

mapping a first set of coordinates representing movements in the virtual reality environment directed by the user with a second set of coordinates specifying locations of the plurality of virtual objects in the virtual reality environment.

10. The virtual environment system of claim 9, wherein the method further comprises:

detecting a trigger action at hand controller sensors configured to track hand movements of the user, the trigger action indicating an identification of one of the plurality of virtual objects, wherein processing the set of sensor data to identify the subset of the plurality of virtual objects interacted with by the user includes both mapping the first set of coordinates with the second set of coordinates and detecting the trigger action.

11. The virtual environment system of claim 10, wherein the method further comprises:

eye tracking sensors disposed in the head-mountable display and configured to track eye movements of the user; and base station sensors disposed in the head-mountable display and configured to track spatial movements of the head-mountable display, wherein the eye tracking sensors and base station sensors are configured to acquire the set of sensor data.

12. The virtual environment system of claim 9, wherein the task comprises an object interaction task, wherein the object interaction task maps movements by the user in the virtual reality environment as matching a location of the virtual objects in the virtual reality environment as specified in the second set of coordinates.

13. The virtual environment system of claim 8, wherein the task comprises an object selection task, wherein the object selection task maps movements by the user in the virtual reality environment to locations comprising virtual objects of a specified virtual object type to identify each virtual object of the specified virtual object type within a scene comprising the plurality of virtual objects.

14. The virtual environment system of claim 8, wherein the first performance metric specifies a performance of the user during each part of the execution of the task, wherein the second performance metric specifies a number and/or magnitude of the spatial movements during each part of the execution of the task, wherein the at least one optical setting is dynamically modified to generate different sub-settings, and wherein each part of the execution of the task corresponds to a different sub-setting.

15. A computer-implemented method comprising:

identifying a task to be executed in a virtual reality environment, where the virtual reality environment is configured to be displayed in a head-mountable display, and where the display of the virtual reality environment includes at least one optical setting that is dynamically modified during execution of the task;

facilitating execution of the task, wherein execution of the task includes displaying a plurality of virtual objects in the display of the virtual reality environment by the head-mountable display;

obtaining, during execution of the task, a set of sensor data from a set of sensors associated with a user;

processing the set of sensor data to map a first set of coordinates in the virtual reality environment representing movements directed by a user with a second set of coordinates specifying locations of the plurality of virtual objects in the virtual reality environment;

deriving a first performance metric based on the mapped coordinates;

processing the set of sensor data to derive spatial movements of the head-mountable display during execution of the task, the spatial movements indicating head movements of the user to interact with the virtual objects during the task;

deriving a second performance metric based on the derived spatial movements; and generating an output based on the first performance metric and the second performance metric, the output representing a functional visual capability of the user to interact with the virtual objects with dynamically modified optical settings in the virtual reality environment.

16. The computer-implemented method of claim 15, wherein the at least one optical setting is dynamically modified from a first setting to a second setting during execution of the task, the optical setting including any of a light intensity setting, a virtual object contrast setting, a dynamically-modified luminance setting, a number of the plurality of virtual objects displayed in the virtual reality environment, a trajectory of movement of the plurality of virtual objects displayed in the virtual reality environment, and locations of the plurality of virtual objects in the virtual reality environment.

17. The computer-implemented method of claim 15, wherein the set of sensors include:

eye tracking sensors disposed in the head-mountable display and configured to track eye movements of the user;

base station sensors disposed in the head-mountable display and configured to track spatial movements of the head-mountable display; and hand controller sensors configured to track hand movements of the user.

18. The computer-implemented method of claim 15, wherein the task is identified from a set of tasks, each task of the set of tasks relates to a particular optical condition relating to the user.

19. The computer-implemented method of claim 15, wherein the task comprises an object selection task, and wherein the object selection task maps movements by the user in the virtual reality environment to locations comprising virtual objects to identify each of the plurality of virtual objects.

20. The computer-implemented method of claim 15, wherein the task comprises an object interaction task, and wherein the object interaction task maps movements by the user in the virtual reality environment as avoiding the location of the virtual objects in the virtual reality environment.

* * * * *